United States Patent
Colman et al.

(10) Patent No.: US 10,194,873 B2
(45) Date of Patent: *Feb. 5, 2019

(54) PERSONALIZED PATIENT ALARM MANAGEMENT

(71) Applicant: ORIDION MEDICAL 1987 LTD., Jerusalem (IL)

(72) Inventors: Joshua Lewis Colman, Jerusalem (IL); Michal Ronen, Givat-Brenner (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/610,289

(22) Filed: May 31, 2017

(65) Prior Publication Data

US 2017/0265819 A1    Sep. 21, 2017

Related U.S. Application Data

(63) Continuation of application No. 14/341,811, filed on Jul. 27, 2014, now Pat. No. 9,706,966.

(51) Int. Cl.
*A61B 5/00* (2006.01)
*G08B 21/04* (2006.01)
*A61B 5/083* (2006.01)

(52) U.S. Cl.
CPC ............ *A61B 5/746* (2013.01); *A61B 5/0836* (2013.01); *G08B 21/0453* (2013.01)

(58) Field of Classification Search
None
See application file for complete search history.

(56) References Cited

U.S. PATENT DOCUMENTS

| | | | |
|---|---|---|---|
| 2006/0047538 A1 | 3/2006 | Condurso et al. | |
| 2007/0293745 A1 | 12/2007 | McCutcheon et al. | |
| 2008/0021731 A1 | 1/2008 | Rodgers | |
| 2010/0121167 A1 | 5/2010 | McGarraugh | |
| 2010/0152544 A1 | 6/2010 | Weaver et al. | |
| 2011/0140896 A1 | 6/2011 | Menzel | |
| 2011/0251468 A1 | 10/2011 | Osorio | |
| 2013/0331660 A1 | 12/2013 | Al-Ali et al. | |
| 2014/0118138 A1 | 5/2014 | Cobelli et al. | |
| 2014/0201627 A1* | 7/2014 | Freeman | G06F 3/04847 715/704 |
| 2014/0253324 A1 | 9/2014 | Tamez | |
| 2014/0275835 A1 | 9/2014 | Lamego et al. | |

OTHER PUBLICATIONS

Baumgartner et al., (2012) A data mining approach to reduce the false alarm rate of patient montiors. Conf Proc IEEE Eng Med Biol Soc 2012: 5935-8.
Bitan et al., (2004) Nurses' reactions to alarms in a neonatal intensive care unit. Cogn Tech Work 6: 239-246.
(Continued)

*Primary Examiner* — Brian Zimmerman
*Assistant Examiner* — Renee Dorsey
(74) *Attorney, Agent, or Firm* — Fletcher Yoder PC (57) ABSTRACT

A personalized patient alarm management profile configured to be used when monitoring one or more medical parameters, the personalized patient alarm management profile determined based on at least two profile determinants.

17 Claims, 7 Drawing Sheets

(56) References Cited

OTHER PUBLICATIONS

Blum et al., (2009) Specificity improvement for network distributed physiologic alarms based on a simple deterministic reactive intelligent agent in the critical care environment. J Clin Monit Comput 23(1): 21-30.

Borowski et al., (2011) Reducing false alarms of intensive care online-monitoring systems: an evaluation of two signal extraction algorithms. Comput Math Methods Med 2011: 143480.

Burgess et al., (2009) Alarm limit settings for early warning systems to identify at-risk patients. J Adv Nurs 65(9): 1844-52.

Charbonnier and Gentil (2007) A trend-based alarm system to improve patient monitoring in intensive care units. Control Engineering Practice 15(9): 1039-1050.

Connor et al., (2009) Triggering of systolic arterial pressure alarms using statistics-based versus threshold alarms. Anaesthesia 64(2): 131-5.

Dherte et al., (2011) Smart alerts: development of software to optimize data monitoring. Rev Bras Anestesiol 61(1): 72-80.

Graham and Cvach (2010) Monitor alarm fatigue: standardizing use of physiological monitors and decreasing nuisance alarms. Am J Crit Care 19(1): 28-34; quiz 35.

Hagenouw (2007) Should we be alarmed by our alarms? Curr Opin Anaesthesia! 20(6): 590-4.

Harrison and Connor (2007) Statistics-based alarms from sequential physiological measurements. Anaesthesia 62(10): 1015-23.

King et al., (2012) Evaluation of a smart alarm for intensive care using clinical data. Conf Proc IEEE Eng Med Biol Soc 2012: 166-9, Feb. 3, 2018.

Li and Clifford (2012) Signal quality and data fusion for false alarm reduction in the intensive care unit. J Electrocardial 45(6): 596-603.

Masimo Patient SafetyNet System. Retrieved from the internet on Jul. 16, 2014.

Taenzer and Blike (2012) Postoperative Monitoring—The Dartmouth Experience. Newsletter. The Official Journal of the Anesthesia Patient Safety Foundation vol. 27, 4 pages.

Taenzer et al., (2010) Impact of pulse oximetry surveillance on rescue events and intensive care unit transfers: a-before-and-after concurrence study. Anesthesiology 112(2): 282-7.

Zong et al., (2004) Reduction of false arterial blood pressure alarms using signal quality assessment and relationships between the electrocardiogram and arterial blood pressure. Med Biol Eng Comput 42(5): 698-706.

\* cited by examiner

PERSONALIZED PATIENT ALARM MANAGEMENT

This application is a continuation of U.S. patent application Ser. No. 14/341,811 filed Jul. 27, 2014, the entire contents of each of which are hereby incorporated by reference.

TECHNICAL FIELD

The present disclosure generally relates to the field of medical device alarms and patient profiles.

BACKGROUND

Medical monitoring devices provide crucial data regarding a patient's medical condition. For example capnographs measure and provide values of the carbon dioxide ($CO_2$) concentration in exhaled breath, and as such may be used to characterize patient's ventilation functioning.

The medical devices are often configured to trigger an alarm alerting health care providers that a monitored parameter deviates from a threshold value. For example, a capnograph may set off an alarm when deviations or changes in the patient's $CO_2$ levels are detected.

SUMMARY

Aspects of the disclosure, in some embodiments thereof, relate to device and methods for providing personalized patient alarm management profile based on the clinical environment, the background characteristics and the treatment profile of a patient. The personalized patient alarm management profile may be configured to determine contextual alarm thresholds and medical parameter display.

Frequent alarms are a common complaint of caregivers. These alarms disrupt clinical workflow, are troubling to the patient and his or her surroundings, and may lead to alarm fatigue amongst the medical personnel. As a consequence thereof, clinically relevant alerts may be overseen, as the alarm is ignored or even turned off, with a possibly tragic outcome.

The device and method for determining a personalized patient alarm management profile, disclosed herein, are configured to take into consideration at least three axes of profile determinants, namely the clinical environment, the background characteristics and the treatment profile of a patient. As a result, a personalized patient alarm management profile may be determined for each patient based on his or hers specific profile determinants, thereby significantly reducing the non-significant alarm frequency. This may on the one hand avoid disruption of clinician workflow while on the other hand increase the clinician's confidence in the remaining alarms, consequently reducing the risk of them failing to notice a clinically significant alert. Thus, the personalized patient alarm management profile, disclosed herein, may provide an alarm management which is safer and more reliable as fewer nuisance alarms are triggered while clinically significant alarms are not overseen.

Nurses or other care-givers can obviously not know which alarm profile to provide for each different patient type, condition etc. Hence in reality, the alarm profiles are defined by department protocols; and nurses, respiratory therapists and even doctors can usually not change the predetermined alarm profile. The personalized patient alarm management profile approach, disclosed herein, is on the one hand safe, as the alarm profile itself is not directly managed by the caregiver, but on the other hand enables patient specificity by enabling the caregiver to input the patient type to a control logic which defines the suitable alarm profile based on the patient type provided.

Moreover, the contextual alarms disclosed herein, may provide the patient and his surrounding a calmer environment with reduced frustration and anxiety resulting from a feeling of being ignored and/or not attended to by the caregivers.

According to some embodiments, there is provided method for determining a personalized patient alarm management profile configured for use in monitoring one or more medical parameters. According to some embodiments, the method includes proving to a processor at least two profile determinants and determining the personalized patient alarm management profile based on the at least two profile determinants. According to some embodiments, the at least two profile determinants include a clinical environment of a patient, a background characteristic of the patient, a treatment profile of the patient or any combination thereof.

According to some embodiments, the clinical environment may include post-anesthesia care unit (PACU), post-operative care unit (Post-OP), emergency department/emergency medical services (ED/EMS), Intensive care unit (ICU), procedural unit, sedation unit, general care unit, pain management unit or combinations thereof.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show structural details of an embodiment in more detail than is necessary for a fundamental understanding of the teachings of the disclosure. For the sake of clarity, some objects depicted in the figures are not to scale.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The present disclosure relates generally to the field of medical device alarms and personalized patient alarm management profile.

There is provided, according to some embodiments, a method for determining a personalized patient alarm management profile configured to be used when monitoring one or more medical parameters, the method comprising: proving to a processor at least two profile determinants; and determining the personalized patient alarm management profile based on the at least two profile determinants.

As used herein, the term "personalized patient alarm management profile" may refer to an alarm management rule configured to set alarm thresholds based on a characterization of the patient, and his or hers clinical surroundings, thereby enabling a patient specific and/or context specific interpretation of monitored medical parameters obtained from the patient. According to some embodiments, the personalized patient alarm management profile may determine a context/patient specific alarm threshold value. According to some embodiments, the personalized patient alarm management profile may determine a context/patient specific display of monitored parameters.

As used herein, the terms "alarm" and "traditional alarm" may interchangeable refer to an alarm configured to be triggered when a medical parameter crosses a predetermined alarm threshold, According to some embodiments, the alarm threshold may be a range, a range that may be a function of time for which the alarm state has been reached, a range that may be a function of by how much the threshold has been passed or any combination thereof. Each possibility is a separate embodiment.

As used herein the terms "contextual alarm threshold" and "contextual alarm threshold value" may refer to an alarm threshold governed by an alarm management rule. Thus, it is understood that the term threshold may refer to a variable rather than a fixed value determined based on the characterization of the patient, and his or hers clinical surroundings. According to some embodiments, the threshold value may be a threshold range. According to some embodiments, the alarm triggered may depend on the alarm management rule, as further described herein. For example, the alarm management rule may determine which parameters generate the alarm. For example, the alarm management rule may determine the threshold for the determined parameters. For example, the alarm management rule may determine the time delay (i.e. the time during which an abnormal value must be obtained before triggering the alarm). For example, the alarm management rule may determine the intensity, amplitude, pitch and/or frequency of the alarm.

According to some embodiment, the alarm may be triggered when a set of medical parameters have all been crossed by a predetermined set of values and/or ranges, as further described herein. The alarm may be an audible alarm configured to alert the clinician.

According to some embodiments, the at least two profile determinants may include a clinical environment of a patient, a background characteristic of the patient, a treatment profile of the patient or any combination thereof. Each possibility is a separate embedment.

According to some embodiments, the at least two profile determinants may be default profile determinants automatically provided to a control logic. According to some embodiments, the at least two profile determinants may be manually provided profile determinants, provided to the control logic by the caregiver for example through a user interface. Optional user interfaces include but are not limited, keyboards, touch screens, mobile phones, remote computers or other suitable user interphases.

As referred to herein, the terms "patient" and "subject" may interchangeably be used and may relate to a subject being monitored by any monitoring device for any physical-condition related parameter and/or health related parameter.

According to some embodiments, the term "clinical environment", as used herein, may refer to the physical surroundings of the patient. Non-limiting examples of possible clinical environments include post-anesthesia care unit (PACU), postoperative care unit (Post-OP), emergency department/emergency medical services (ED/EMS), intensive care unit (ICU), procedural unit, sedation unit, general care unit, pain management unit or combinations thereof. Each possibility is a separate embodiment.

It is understood to one of ordinary skill in the art that different clinical environments may require a different alarm sensitivity. For example, patients in an operating room who are sedated and under constant medical attention may require a different alarm sensitivity than patient in a post-operative care unit which may often be able to move around and who do not receive constant medical attention.

According to some embodiments, the term "background characteristic", as used herein, may refer to patient specific parameters. Non-limiting examples of optional background characteristics include: generally healthy, chronic obstructive pulmonary disease (COPD), obstructive sleep apnea (OSA), asthma, chronic heart failure (CHF), low base-line peripheral capillary oxygen saturation ($SpO_2$), head injury, age, sex, weight or any combination thereof. Each possibility is a separate embodiment.

According to some embodiments, the term "treatment profile", as used herein, may refer to the treatment provided to a specific patient. Non-limiting examples of optional treatment profiles include: oxygen supply, intubated, non-invasive intubation, non-intubated, medication (e.g., beta-agonist), machine ventilation, bagged, sedation, analgesia, $CO_2$ insufflation, or any combination thereof. Each possibility is a separate embodiment.

As used herein, the term "at least two" when referring to profile determinants, may include 2, 3, 4, 5 or more threshold determinants. Each possibility is a separate embodiment.

It is understood by one of ordinary skill in the art that any of the profile determinants—clinical environment, background characteristic and treatment profile—may include more than one parameter. The patient may for example receive oxygen supply through a ventilation tube (thus both oxygen supply and machine ventilation are parameters of the treatment profile). Similarly, the patient may have several patient characteristics, age (e.g. 70), OSA and asthma being one non-limiting example. On the other hand, some parameters may be mutually exclusive. The patient can for example not be classified as generally healthy if suffering from CHF.

It is further understood that some parameters are binary parameters (for example the patient either has or has not a head injury), whereas other parameters are continuous (for example the age of the patient). Additionally, some parameters may be both binary and continuous. For example, the weight of the patient may be binary parameter (obese/nonobese) or continuous (the exact weight of the patient). According to some embodiments, some parameters may be may be classified according to categories. For example the weight of the patient may be classified as being underweight, normal weight, overweight, obese, severely obese or morbidly obese.

According to some embodiments, at least one of the at least two profile determinants may be fixed. As a non-limiting example, a monitor may be permanently situated in postoperative care unit and thus the clinical environment of the monitor may be permanent/fixed.

According to some embodiments, the medical parameter may be a monitored parameter. According to some embodiments, the medial parameter may be a parameter derived from or calculated from the monitored parameter. According to some embodiments, the medical parameter may be a parameter derived from an integration of a plurality of monitored and/or calculated parameters. According to some embodiments, the medical parameter may be a trend computed from a monitored medical parameter, a trend computed from a medical parameter derived from a monitored parameter and/or a trend computed from a medical parameter derived from an integration of a plurality of monitored parameters. Each possibility is a separate embodiment.

According to some embodiments, the medical parameter may include a $CO_2$ related parameter, a ventilation related parameter, respiration rate (RR), an oxygen related parameter, heart rate (HR), an electrocardiogram (ECG), an encephalogram (EEG), blood pressure, spirometry, level of consciousness, level of sedation or any combination thereof. Each possibility is a separate embodiment.

According to some embodiments, the $CO_2$ related parameter may include a $CO_2$ waveform related parameter, an expired air $CO_2$ concentration, respiratory rate or any combination thereof. Each possibility is a separate embodiment.

According to some embodiments, the oxygen related parameter may be percentage of oxygen saturation ($SpO_2$). According to some embodiments, the oxygen related parameter may be a SatSec parameter. As used herein, the term "SatSec parameter" may refer to a multiplication of the deviation in the percentage of oxygen saturation and the length of time during which the deviation persist. For example, if the saturation limit is 92 percent and the patient's $SpO_2$ drops to 86 percent for two seconds before the saturation returns above the low alarm limit of 92 percent, the SatSet parameter is 12 SatSecs. According to some embodiments, the saturation limit may be set to 90 percent or above, 92 percent or above; or 95% $SpO_2$ or above. Each possibility is a separate embodiment. According to some embodiments, the saturation limit may be set to 20, 25, 30, 40, 50, 60, 70, 75, 80 SatSecs or above. Each possibility is a separate embodiment. According to some embodiments, a higher $SpO_2$ reference value (e.g. above 90 percent and/or below 50 SatSecs) may be used when the patient receives oxygen supply.

According to some embodiments, the oxygen related parameter may be a saturation pattern detection (SPD) parameter. According to some embodiment, the SPD parameter may be indicative of a repetitive reduction in airflow. According to some embodiments, the SPD may be used for the detection of sleep apnea.

According to some embodiments, the oxygen related parameter may include respiration rate.

According to some embodiments, the oxygen related parameter may include breathing effort. As used herein the terms "breathing effort" may refer to the physical effort or work of breathing. The breathing effort may affect respiratory signals, such as, but not limited to, a PPG signal. Respiratory effort may increase, for example, if a patient's respiratory pathway becomes restricted or blocked. Conversely, respiratory effort may decrease as a patient's respiratory pathway becomes unrestricted or unblocked.

According to some embodiments, the medical parameter may include an algorithmically-derived index of multiple parameters. As used herein, the term "algorithmically-derived index of multiple parameters" may refer to a unit less index value representative of a plurality of medical parameters. According to some embodiments, the algorithmically-derived index of multiple parameters may be computed by:

(a) characterizing a first measured medical parameter based on a comparison of the first measured medical parameter against a first reference value;

(b) characterizing a second measured medical parameter based on a comparison of the second measured medical parameter against a second reference value; and (c) computing the index value based on values associated with each of the characterized first and second measured medical parameters.

According to some embodiments the first and second measured medical parameters may be any of the medical parameters listed above.

According to some embodiments, the medical parameter may include more than one medical parameter. For example, the medical parameter may include 2, 3, 4, 5, 10 or more parameters. Each possibility is a separate embodiment.

According to some embodiments, the method may further include adjusting the personalized patient alarm management profile based on a change in one or more of the at least two profile determinants. According to some embodiments, the method may further include adjusting a contextual alarm threshold value based on a change in one or more of the at least two profile determinants and consequently in the personalized patient alarm management profile. According to some embodiments, adjusting a personalized patient alarm management profile and/or a contextual alarm threshold may include desensitizing the alarm profile, so that only if deterioration occurs, the alarm is triggered.

According to some embodiments, the change in the one or more profile determinants may be based on measurements of a (same or other) medical parameter, on an obtained alarm pattern or a combination of both. Each possibility is a separate embodiment. According to some embodiments, the profile determinants may change during the hospitalization of the patient. As a non-limiting example, the patient may initially be bagged whereafter oxygen supply is provided by an oxygen mask. Accordingly, the treatment profile (and as a result thereof, the personalized patient alarm management profile) may change from oxygen supply—bagged, to oxygen supply—non-intubated. As an additional non-limiting example, patients are often unaware of certain background characteristics, such as, but not limited to, the fact that they are suffering from OSA. OSA is therefore often initially not indicated as a background characteristic provided to the control logic. OSA may be discovered during the hospitalization of the patient for example as a result of frequent recurring alarms when the patient is asleep, as a result of repeated desaturations and apneas and/or as a result to indications obtained from Apnea Saturation Alerts (ASA) and Saturation Pattern Detection (SPD). Accordingly, the background characteristic (and as a result thereof, personalized patient alarm management profile) may be adjusted by adding OSA, as an additional/alternative background characteristic. According to some embodiments, adjusting the personalized patient alarm management profile, as a result of detecting OSA, may include changing settings relating to desaturations and/or apnea events to trigger an alarm only if the frequencies, amplitude and/or duration of the desaturations and/or apnea events have increased or become more severe (i.e., when the condition worsens).

It is understood by one of ordinary skill in the art that the adjustment of the personalized patient alarm management profile may be manual (e.g. by the nurse or other caregiver). Additionally or alternatively, the adjustment may be automatic, for example based on a detection of a change in patient "background characteristic" by the control logic of the monitor.

According to some embodiments, the personalized patient alarm management profile may determine a contextual alarm threshold which when crossed may trigger an alarm. According to some embodiment, the alarm threshold may be a threshold range. According to some embodiments, the personalized patient alarm management profile may determine an incremental time factor applied to an alarm threshold value. According to some embodiments, the values within the threshold range may be weighted by an incremental time factor. Alarm thresholds are typically used to define a border between a normal status and a status which is perceived as a risk. However, typically there are no real differences between values just below the defined border as opposed to those just above the defined border. Moreover, those defining the threshold tend to prefer oversensitive threshold values in order to minimize the risk, despite the high rate of nuisance alarms as a result thereof. Providing an alarm range, instead of defining discrete alarm threshold values, may enable to add a sensitivity assessment to each point within the range, for example by adding a "relative duration" as a second factor for triggering the alarm. In effect, a value at the top of the range may result in an immediate triggering of the alarm, whereas a value at the bottom of the range may result in a triggering of the alarm only if the measure medical parameter crosses the value for a predetermined period of time, i.e. after a predetermined time delay. The net result is an overall reduction in the sensitivity of the alarm and thus a reduction in nuisance alarms.

According to some embodiments, the personalized patient alarm management profile may determine sub-ranges within a threshold range. According to some embodiments, the threshold range may include a coarse threshold region and a tunable threshold sub-region. Typically, the medical care giver who defines alarm thresholds may not be the nurse attending the patient. In fact, usually the nurse has no ability to change an alarm setting even if determined to be oversensitive for a particular patient. According to some embodiments, the personalized patient alarm management profile may determine a bi-level alarm threshold with coarse and fine tuning which may on the hand assure that the responsible medical care giver coarsely defines an (broad) alarm thresholds region, and which on the other hand permits the nurse to perform fine tuning within the defined region, for example by elevating a lower limit of the alarm range. According to some embodiments, the coarse threshold region may be a fixed threshold region provided by the manufacturer of the monitor or determined by suitable medical boards.

According to some embodiments, the personalized patient alarm management profile may determine an alarm range and a notification range. According to some embodiment, the threshold range may include an alarm range and a notification range. As used herein, the term "notification range" may refer to an audible alert (distinguishable from the alarm), a text message or any other suitable means to notify the primarily the patient and/or his relatives that "out-of-normal" measurement are received.

According to some embodiments, the method may also include determining a notification threshold based on the personalized patient alarm management profile and thus the at least two threshold determinants. It is understood by one of ordinary skill in the art that the personalized patient alarm management profile may determine a notification value (or range) which may be more sensitive than the contextual alarm threshold value (or range), such that a notification may be provided at values closer to normal than the values triggering the alarm. For example, the personalized patient alarm management profile may be configured to include a notification alert, when a patient is identified as suffering from OSA. The notification alert may induce the OSA patient to breathe and thereby avoid triggering the traditional alarm.

According to some embodiments, there is provided a user interphase configured to determine a personalized patient alarm management profile for use when monitoring one or more medical parameters. According to some embodiments, the user interface may include two or more profile determinants.

According to some embodiments, at least one of the two or more profile determinants may include user selectable profile options. As used herein, the term "at least one" with regards to user selectable options may include 1, 2, 3, 4, 5, 10 or more options. Each possibility is a separate embodiment. According to some embodiments, the number of options may be within the range of 1-15 options. Each number within the range is a separate embodiment. According to some embodiments, the user selectable options may be multiple exclusive. According to some embodiments, the user selectable options may be cumulative.

According to some embodiments, at least one of the two or more user selectable profile options may be fixed. As used herein, the term "fixed", with regards to user selectable options may refer to a profile determinant options predetermined by the manufacturer, by a medical board or by a caregiver, whereafter the profile determinant option remain unchanged.

According to some embodiments, the at least two profile determinants may include a clinical environment of a patient, a background characteristic of the patient, a treatment profile of the patient or any combination thereof. Each possibility is a separate embedment.

According to some embodiments, the term "clinical environment", as used herein, may refer to the physical surroundings of the patient. According to some embodiments, user selectable options for the clinical environment may include post-anesthesia care unit (PACU), postoperative care unit (Post-OP), emergency department/emergency medical services (ED/EMS), intensive care unit (ICU), procedural unit, sedation unit, general care unit, pain management unit or combinations thereof. Each possibility is a separate embodiment.

According to some embodiments, the term "background characteristic", as used herein, may refer to patient specific parameters. According to some embodiments, user selectable options for background characteristics include: generally healthy, chronic obstructive pulmonary disease (COPD), obstructive sleep apnea (OSA), asthma, chronic heart failure (CHF), low base-line peripheral capillary oxygen saturation ($SpO_2$), head injury, age, sex, weight or any combination thereof. Each possibility is a separate embodiment.

According to some embodiments, the term "treatment profile", as used herein, may refer to the treatment provided to a specific patient. According to some embodiments, user selectable options for treatment profiles include: oxygen supply, intubated, non-invasive intubation, non-intubated, medication (e.g., beta-agonist), machine ventilation, bagged, sedation, analgesia, $CO_2$ insufflation, or any combination thereof. Each possibility is a separate embodiment.

As used herein, the term "at least two" when referring to profile determinants, may include 2, 3, 4, 5 or more threshold determinants. Each possibility is a separate embodiment.

According to some embodiments, the user interface may include a keyboard, a touch screens, a mobile phone, a computers a laptop or any other suitable user interphase. Each possibility is a separate embodiment.

According to some embodiments, the user interface may include a processor. According to some embodiments, the processor may be configured to determine the personalized patient alarm management profile based on the at least one provided user selectable option provided for each of the at least two profile determinants. According to some embodiments, the processor may be configured to compute and/or set a contextual alarm threshold value based on the determined personalized patient alarm management profile.

According to some embodiments, the user interface may be further configured to allow adjustment of the personalized patient alarm management profile, based on a change in one or more of the at least two profile determinants. According to some embodiments, the user interface may allow a caregiver to change and/or modify at least one user selectable option of at least one of the two or more profile determinants. According to some embodiments, the change in the one or more user selectable options may be made due to an explicit change, such as, but not limited to, a change in the treatment of the patient (e.g. from non-intubated to intubate). Additionally or alternatively, the change in the one or more user selectable options may be made due to an assessment of the medical parameters monitored (e.g. identifying the patient as suffering from OSA).

According to some embodiments, the processor may be configured to adjust a configuration of the alarm (e.g. adding a notification alert) based on the personalized patient alarm management profile.

According to some embodiments, the user interface may include a display configured to display the at least two profile determinants and the user selectable options for each profile determinant. According to some embodiments, the display may further be configured to display the determined personalized patient alarm management profile. For example, the display may display the characteristic of the hospitalization. Non-limiting examples of suitable characteristics include short term and long term hospitalization. Each possibility is a separate embodiment. For example, the display may display the main concern with regards to the hospitalization. Non-limiting examples include risk of apnea events, risk of low quality $CO_2$ signal, risk of desaturation at high SpO2 values and the like. Each possibility is a separate embodiment. For example, the display may display the required features with regards to the monitoring of the patient. Non-limiting examples of suitable required features include presence/absence of breaths, respiration rate, $CO_2$ waveform, pleth wave, nuisance parameters and the like. Each possibility is a separate embodiment. For example, the display may display the proposed alarm profile for the monitored parameters. Non-limiting examples include single parameter thresholds and/or threshold ranges, index parameter thresholds and/or threshold ranges, notification thresholds, alarm configuration and the like. Each possibility is a separate embodiment.

According to some embodiment, there is provided a control logic configured to receive a measured medical parameter of a patient; compare the measured medical parameter to a contextual threshold value; and to trigger an alarm when the measured medical parameter crosses the contextual threshold value. As used herein, the term "control logic", may refer to a computer, a computer program or other processing element configured to receive inputs (e.g. measured medical parameters), perform an operation (e.g. compare the measured medical parameter to a contextual threshold value) and provide outputs (e.g. trigger an alarm).

According to some embodiment, the contextual alarm threshold value may be determined according to a personalized patient alarm management profile as essentially described hereinabove. According to some embodiments, the personalized patient alarm management profile may be determined based on at least two profile determinants.

According to some embodiments, the at least two profile determinants may include a clinical environment of a patient, a background characteristic of the patient and/or a treatment profile of the patient.

According to some embodiments, the clinical environment may include post-anesthesia care unit (PACU), post-operative care unit (Post-OP), emergency department/emergency medical services (ED/EMS), intensive care unit (ICU), procedural unit, sedation unit, general care unit, pain management unit or combinations thereof. Each possibility is a separate embodiment.

According to some embodiments, the background characteristic may include: generally healthy, chronic obstructive pulmonary disease (COPD), obstructive sleep apnea (OSA), asthma, chronic heart failure (CHF), low base-line spo2, head injury, age, sex, weight or any combination thereof. Each possibility is a separate embodiment.

According to some embodiments, the treatment profile may include: oxygen supply, $CO_2$ insufflation, intubated, non-invasive intubation, non-intubated, medication (e.g., beta-agonist), machine ventilation, bagged, sedation, analgesia or any combination thereof. Each possibility is a separate embodiment.

According to some embodiments, the control logic may be configured to adjust the personalized patient alarm management profile (and thus the contextual threshold value) based on a change in one or more of the at least two profile determinants. According to some embodiments, the change in the one or more threshold determinants may be based on measurements of a (same or other) medical parameter, on an obtained alarm pattern or a combination of both, as essentially described hereinabove.

It is understood by one of ordinary skill in the art that the adjustment of the personalized patient alarm management profile and/or the contextual alarm threshold may be manual (e.g. by the nurse or other caregiver). Additionally or alternatively, the adjustment may be automatic, for example based on a detection of a change in patient "background characteristic" by the control logic of the monitor.

According to some embodiments, the control logic may be configured to detect OSA. OSA may be discovered during the hospitalization of the patient for example as a result of frequent recurring alarms when the patient is asleep, as a result of repeated desaturations and apnea and/or as a result to indications obtained from ASA and SPD. OSA patient are characterized by on the one hand suffering from frequent low-risk apneas which tend to cause nuisance alarms, and on the other hand by having an elevated sensitivity of the ventilatory system to the effects of analgesia, which put them in a high risk group. Accordingly, defining specific alarm settings for OSA patients is of uttermost importance for identifying true risks amongst the numerous events of apnea which do not necessarily require medical attention.

According to some embodiments, the control logic may be configured to take into consideration the influence of a medical procedure on a monitored parameter. As a non-limiting example, a patient undergoing a gastro-intestinal procedure, such as, but not limited to, Endoscopic retrograde cholangiopancreatography (ERCP), has typically his stomach and digestive tract insufflated with $CO_2$. The $CO_2$ supplied to the stomach may escape, and as a result thereof, cause erroneously high $EtCO_2$ measurements, which in turn may lead to incorrect triggering of alarms. The control logic, disclosed herein, may be configured to correct $CO_2$ measurements for $CO_2$ originating from the insufflated stomach, if it is known that the patient is insufflated with $CO_2$.

According to some embodiments, the control logic may be configured to adjust the personalized patient alarm management profile based on a patient provided input. For example, the control logic may be configured to turn off the alarm as a response to the patient indicating removal of a patient interface and/or sensor. According to some embodiments, the control logic may be configured to adjust the personalized patient alarm management profile based on an indication that the patient interface and/or sensor has been removed from the patient. According to some embodiment, the patient interface and/or sensor may include a feature configured to detect removal of the interface/sensor. According to some embodiments, the patient interface may include any element configured to be worn or otherwise connected to the patient thereby facilitating monitoring of medical parameters.

According to some embodiments, the determined contextual alarm profile may be a threshold range. According to some embodiments, the values within the threshold range may be weighted by an incremental time factor, as essentially described hereinabove.

According to some embodiments, the threshold range may include a coarse threshold region and a tunable threshold sub-region, as essentially described herein above.

According to some embodiments, the medical parameter may be a monitored parameter. According to some embodiments, the medial parameter may be a parameter derived from or calculated from the monitored parameter. According to some embodiments, the medical parameter may be a parameter derived from an integration of a plurality of monitored and/or calculated parameters. According to some embodiments, the medical parameter may be a trend computed from a monitored medical parameter, a trend computed from a medical parameter derived from a monitored parameter and/or a trend computed from a medical parameter derived from an integration of a plurality of monitored parameters. Each possibility is a separate embodiment.

According to some embodiments, the control logic may be configured to compute a trend in the measured medical parameter. According to some embodiments, the trend may be computed based on medical parameters obtained during a predetermined time window. According to some embodiments, the trend may be computed as a moving average of the medical parameters obtained during a predetermined time window. According to some embodiments, the predetermined time window may be a variable time window. According to some the length of the variable time window may be determined based on the variability in the measured medical parameter. According to some embodiments, the length of the time window may be increased when the variability is high and reduced when the variability of the measured medical parameter is low.

According to some embodiments, the medical parameter may include a $CO_2$ related parameter, ventilation related parameters, respiration rate (RR), an oxygen related parameter, heart rate (HR), an electrocardiogram (ECG), an encephalogram (EEG), blood pressure, spirometry, level of consciousness, level of sedation or any combination thereof. Each possibility is a separate embodiment.

According to some embodiments, the $CO_2$ related parameter may include a $CO_2$ waveform related parameter, an expired air $CO_2$ concentration, respiratory rate or any combination thereof. Each possibility is a separate embodiment.

According to some embodiments, the medical parameter may include an algorithmically-derived index of multiple parameters. According to some embodiments, the algorithmically-derived index of multiple parameters may be computed by:

(a) characterizing a first measured medical parameter based on a comparison of the first measured medical parameter against a first reference value;

(b) characterizing a second measured medical parameter based on a comparison of the second measured medical parameter against a second reference value; and (c) computing the index value based on values associated with each of the characterized first and second measured medical parameters.

According to some embodiments the first and second measured medical parameters may be any of the medical parameters listed above. According to some embodiments, the algorithmically-derived index of multiple parameters may be an adaptive index governed by the personalized patient alarm management profile. According to some embodiments, the personalized patient alarm management profile and thus the adaptive index may be configured to take into consideration changes in $SpO_2$ reference values. According to some embodiments, the personalized patient alarm management profile and thus the adaptive index may use an $SpO_2$ reference value of 90 percent. According to some embodiments, the personalized patient alarm management profile and thus the adaptive index may use an $SpO_2$ reference value of above 90% (e.g. 92%). According to some embodiments, the personalized patient alarm management profile may be configured to determine a higher $SpO_2$ reference value (e.g. above 90) when the patient receives oxygen supply. When the patient receives oxygen supply, the personalized patient alarm management profile should take into consideration that reduction in oxygen saturation may occur at higher saturation values. Consequently, the contextual alarm threshold value determined by the personalized patient alarm management profile should preferably be adjusted to be more sensitive to de-saturation for example by elevating the threshold value to 92 percent.

According to some embodiments, the medical parameter may include more than one medical parameter. For example, the medical parameter may include 2, 3, 4, 5, 10 or more parameters. Each possibility is a separate embodiment.

According to some embodiments, the control logic may be configured to display the measured and/or computed medical parameter, a trend in the measured and/or computed medical parameter or both on a display. According to some embodiments, when the medical parameter is algorithmically-derived index of multiple parameters, the control logic may be configured to display which of the multiple parameters of the parameter led to triggering of the alarm.

According to some embodiments, the displayed medical parameter may be determined by the personalized patient alarm management profile. As a non-limiting example, a normally healthy patient, in a procedural unit, sedation care unit, receiving analgesia and sedation has an elevated risk of absence of breathing and low respiration rate (RR), thus the $CO_2$ waveform, the pleth-wave (or other indication of $SpO_2$ quality) should preferably be displayed, As another non-limiting example, OSA patients are characterized by on the one hand suffering from frequent low-risk apneas which tend to cause nuisance alarms, and on the other hand by having an elevated sensitivity of the ventilatory system to the effects of analgesia which put them in a high risk group. Accordingly, the frequency of desaturations and/or apnea events, the amplitudes and their durations may preferably be displayed.

According to some embodiments, the control logic may be configured to provide a history of measured medical parameters. According to some embodiments, the history of measured medical parameters may be computed based on measured medical parameters obtained during a predetermined time period prior to the alarm being triggered. When an alarm is triggered, the origin of the alarm is not always clear i.e. which events led to the alarm. According to some embodiments, the history of measured and/or computed medical parameters include trend information (trend history) which relates to the events and parameters as they progressed into the alarm state. According to some embodiments, displaying the history of measured and/or computed medical parameters, which led to the alarm state, may enable the caregiver to immediately assess which events and deviation in the measured and/or computed medical parameters led to the alarm state and their clinical significance.

According to some embodiments, the control logic may be configured to compute an anticipated patient status based on the personalized patient alarm management profile and on the measured and/or computed medical parameter. According to some embodiments, computing the anticipated patient status further includes comparing the measured and/or computed medical parameter and/or the trend therein to a dataset of medical parameters obtained for patients (the same patient at different time points or different patient sharing the same personalized patient alarm management profile) prior to them deteriorating into a critical state. According to some embodiments, computing the anticipated patient status may further include providing a reliability score for the anticipated patient status. According to some embodiments, the reliability score may be calculated based on a statistical analysis of the dataset of obtained medical parameters. It is understood to one of ordinary skill in the art, that the anticipated patient status may enable the caregiver to react and possibly even prevent the deterioration of the patient into a critical state.

According to some embodiments, the control logic may be configured to provide a clinical recommendation and/or instructions to the caregiver, the patient and/or his relatives. According to some embodiments, the clinical recommendation and/or instructions to the caregiver may be based on the personalized patient alarm management profile and on the measured and/or computed medical parameter. According to some embodiments, the clinical recommendation may serve as a preemptive measure configured to avoid deterioration of the patient into a critical state. According to some embodiments, the clinical recommendation may be based on the personalized patient alarm management profile. According to some embodiments, the clinical recommendation may be based on the anticipated medical status of the patient.

According to some embodiments, the clinical recommendation may serve as a reactive measure as a result of a deterioration of the patient into a critical state According to some embodiments, the clinical recommendation may be based on the history of measured and/or computed medical parameters of the patient. According to some embodiments, the clinical recommendation may be a reactive clinical recommendation based on the history of measured medical parameters. According to some embodiments, the recommendation may be based on identification of a patient characteristic, such as, but not limited to, OSA. Suitable recommendations include, but are not limited to: use continuous positive airway pressure (CPAP), add oxygen supply or any other suitable recommendation. Each possibility is a separate embodiment.

According to some embodiments, the clinical recommendation may include technical and/or clinical instructions i.e. alerts due to device-related issues. A non-limiting example of a clinical instruction includes "check airways". A non-limiting example of a technical instruction includes "verify sensor connection". According to some embodiments, the clinical recommendation may include a treatment recommendation, based on a computed trend of the medical parameter. According to some embodiments, the clinical recommendation may include a treatment recommendation, based on an anticipated patient status.

According to some embodiments, the control logic may be configured to control the operation of a ventilation machine based on the personalized patient alarm management profile and/or on a measured/computed medical parameter (or trend therein). Each possibility is a separate embodiment.

According to some embodiments, there is provided a medical device including a control logic and an alarm. According to some embodiments, the control logic may be configured to receive a measured medical parameter of a patient; compare the measured medical parameter to a contextual alarm threshold value and to trigger the alarm when the measured medical parameter crosses the contextual alarm threshold value.

According to some embodiments, the contextual threshold value may be determined according to a personalized patient alarm management profile, as essentially described herein.

According to some embodiment, the personalized patient alarm management profile and thus the contextual alarm threshold may be determined based on at least two profile determinants. According to some embodiments, the at least two profile determinants include a clinical environment of a patient, a background characteristic of the patient and a treatment profile of the patient.

According to some embodiments, the clinical environment comprises post-anesthesia care unit (PACU), postoperative care unit (Post-OP), emergency department/emergency medical services (ED/EMS), intensive care unit (ICU), procedural unit, sedation unit, general care unit, pain management unit or combinations thereof. Each possibility is a separate embodiment.

According to some embodiments, the background characteristic may include: generally healthy, chronic obstructive pulmonary disease (COPD), obstructive sleep apnea (OSA), asthma, chronic heart failure (CHF), low base-line SpO2, head injury, age, sex, weight or any combination thereof. Each possibility is a separate embodiment.

According to some embodiments, the treatment profile may include: oxygen supply, intubated, non-invasive intubation, non-intubated, medication (e.g., beta-agonist), machine ventilation, bagged, sedation, analgesia, $CO_2$ insufflation, or any combination thereof. Each possibility is a separate embodiment.

According to some embodiments, the medical device may include a color display configured to display the measured medical parameter and/or a trend therein. According to some embodiments, the medical parameter and/or trend displayed may be determined based on the personalized patient alarm management profile. According to some embodiments, the display may display the measured medical parameter or the trend therein in a first color when within a normal range and in a second color when out of normal range. According to some embodiments, the first color may be green. According to some embodiments, the second color may be red. As known to the ordinary skilled in the art, monitors today typically display a vast amount of information, each depicted in its own color. As a result, when an alarm is sounded, it is not always obvious which value on the screen triggered the alarm or which part of a depicted trend includes the area of interest. According to some embodiments, the display, disclosed herein, may be configured to depict all normal values in a first color (e.g. green) and values out of range in a second color (e.g. red). According to some embodiments, when a measured medical parameter reaches a level requiring caution, the value may turn yellow, and only when reaching an alarm (risk) level, it may turn red. Similarly, green, yellow and red colors may be used to define regions within the trend.

According to some embodiments, the alarm may include an audible severity indication. According to some embodiments, the severity indication may be determined by the personalized patient alarm management profile. It is known that alarm amplitude, pitch or frequency may not be easily translated into severity levels and not always appreciated equally between different caregivers. However, a change in alarm amplitude, pitch or frequency when used with reference to a base alarm amplitude, pitch or frequency may serve as an objective audible severity indication. According to some embodiments audible severity indication includes providing pitch changes between consecutive beats in the audible alarm. In this way, when alternating between two levels for consecutive beats, the changes in the pitch are more easily recognized.

According to some embodiments, the alarm may be triggered based on an anticipation of a patient's status. According to some embodiments, the anticipated patient status may be based on the personalized patient alarm management profile and on the measured medical parameter. According to some embodiments, computing the anticipated patient status may further be based on a comparison of the measured medical parameter and/or the trend therein to a dataset of medical parameters obtained for patients (the same patient at different time points or different patients sharing the same personalized patient alarm management profile) prior to them deteriorating into a critical state. It is thus understood to one of ordinary skill in the art, that triggering the alarm based on an anticipation of the patient's status may enable the caregiver to react and thereby possibly prevent the deterioration of the patient into a critical state. According to some embodiments, the alarm triggered based on an anticipation of the patient's status may be different from the traditional alarms, such as but not limited to a voice message or an audible sound distinct from the traditional alarm. According to some embodiments, the control logic may be configured to provide a preemptive clinical recommendation based on the anticipated patient status.

According to some embodiments, the alarm may include an alerts-disable option. According to some embodiments, the alert-disable option enables the patient or a person attending the patient or the medical care-giver to turn off the alarm when sensors are removed.

Figure 1:
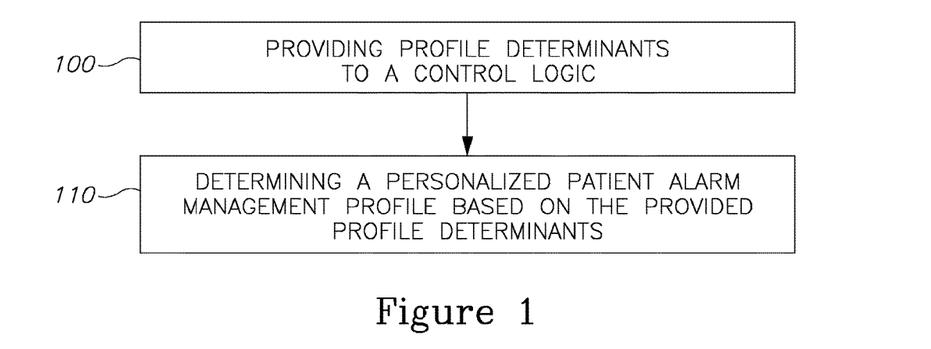
FIG. 1 is an illustrative flowchart of the method for determining a personalized patient alarm management profile, according to some embodiments.

Reference is now made to FIG. 1 which is an illustrative flowchart of the method for determining a personalized patient alarm management profile, according to some embodiments. At step 100, at least two profile determinants (clinical environment, medical characteristic and treatment profile) are provided to a control logic, and at step 110, a personalized patient alarm management profile is determined based on the at least two profile determinants. Optionally, the determined personalized patient alarm management profile may be adjusted as a result of changes in one or more of the threshold determinants, as essentially described hereinabove.

Figure 2:
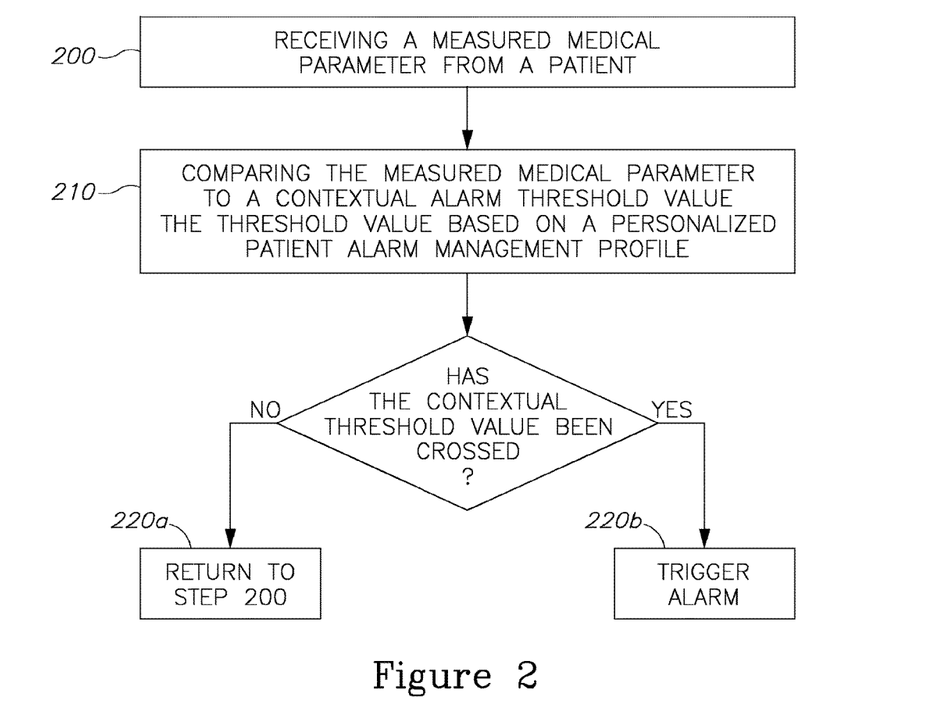
FIG. 2 is an illustrative flowchart of the operation of a control logic, according to some embodiments.

Reference is now made to FIG. 2 which is an illustrative flowchart of the operation of a control logic, according to some embodiments. At step 200, the control logic receives a measured medical parameter of a patient. Suitable medical parameters are disclosed herein. At step 210, the control logic compares the measured medical parameter to a contextual alarm threshold value. The contextual alarm threshold value is determined based on a personalized patient alarm management profile determined by an integration of at least two threshold determinants, as essentially described herein. Has the contextual alarm threshold value not been crossed, no action is triggered and the control logic returns to step 200, as described in step 220a. Has the contextual alarm threshold value been crossed, the control logic triggers the alarm, as described in step 220b.

As described herein, the control logic is configured to adjust the personalized patient alarm management profile (either manually or automatically) as a result of changes in one or more of the profile determinants. It is understood by one of ordinary skill in the art that such adjustment can be carried out at any stage of the operation of the control logic. For example, the adjustment may be carried out as a result of an excessive triggering of the alarm, and identification of OSA. Optionally, has OSA been detected, a screen may be provided that shows (e.g. graphically), the frequency of the desaturations and or apnea events, the amplitudes and their durations.

Figure 3:
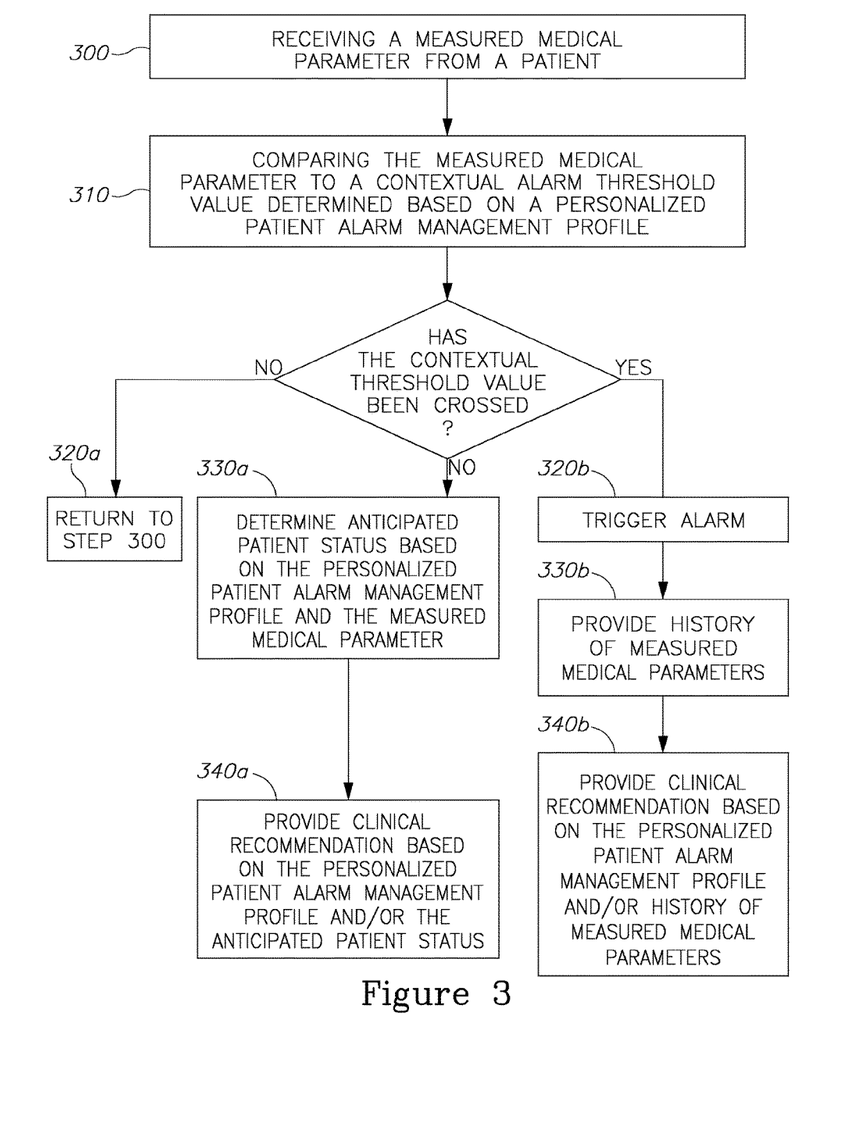
FIG. 3 is an illustrative flowchart of the operation of a control logic, according to some embodiments.

Reference is now made to FIG. 3 which is an illustrative flowchart of the operation of a control logic, according to some embodiments. At step 300, the control logic receives a measured medical parameter of a patient. Suitable medical parameters are disclosed herein. At step 310, the control logic compares the measured medical parameter to a contextual alarm threshold value. The contextual alarm threshold value is determined based on a personalized patient alarm management profile determined by an integration of at least two profile determinants, as essentially described herein. Has the contextual alarm threshold value not been crossed, no action is triggered and the control logic returns to step 300, as described in step 320a. In step 330a, the control logic further provides an anticipated patient status, based on the personalized patient alarm management profile and the measured medical parameter. Optionally, in step 340a the control logic may also provide a clinical recommendation and/or instruction to the caregiver, the patient and/or his relatives, based on the personalized patient alarm management profile and/or the anticipated medical status. Has the contextual alarm threshold value been crossed, the control logic triggers the alarm, as described in step 320b. Furthermore, in the event of an alarm, the control logic may provide a history of measured medical parameters, as described in step 330b. The history of measured medical parameters may be based on measured medical parameters obtained during a predetermined time period prior to the alarm being triggered. Optionally, in step 340b the control logic may provide a clinical recommendation and/or instruction to the caregiver, the patient and/or his relatives, based on the personalized patient alarm management profile and/or the history of measured medical parameters.

As described herein, the control logic is configured to adjust the personalized patient alarm management profile and/or the alarm threshold as a result of changes in one or more of the profile determinants. It is understood by one of ordinary skill in the art that such adjustment can be carried out at any stage of the operation of the control logic. For example, the adjustment may be carried out as a result of an excessive triggering of the alarm, and identification of OSA.

Figure 4:
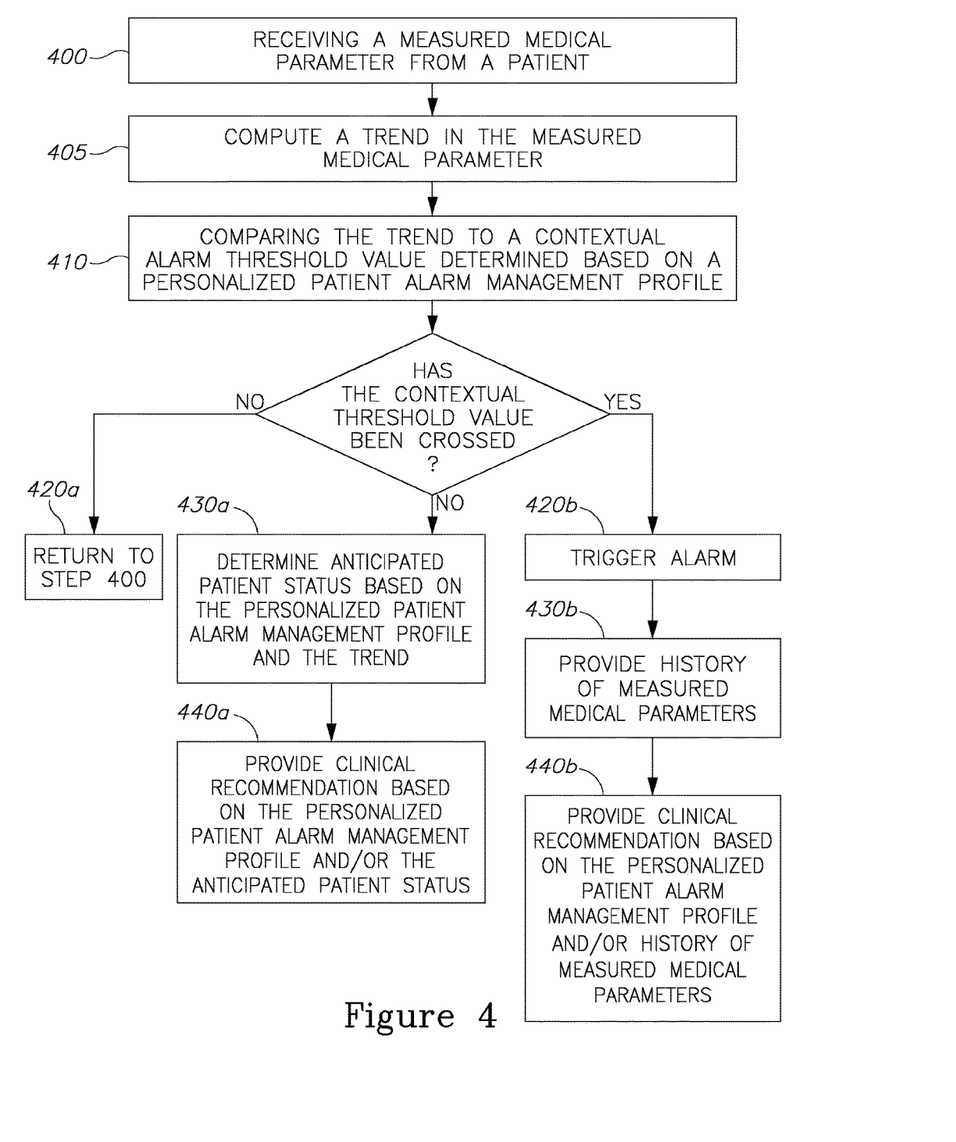
FIG. 4 is an illustrative flowchart of the operation of a control logic, according to some embodiments.

Reference is now made to FIG. 4 which is an illustrative flowchart of the operation of a control logic, according to some embodiments. At step 400, the control logic receives a measured medical parameter of a patient. Suitable medical parameters are disclosed herein. At step 405, the control logic may be configured to compute a trend in the measured medical parameter, based on the measured parameters received in step 400. According to some embodiments, the trend may be computed as a moving average of the medical parameters obtained during a predetermined time window. At step 410, the control logic compares the trend to a contextual alarm threshold value. The contextual alarm threshold is determined based on a personalized patient alarm management profile determined by an integration of at least two profile determinants, as essentially described herein. Has the contextual alarm threshold value not been crossed, no action is triggered and the control logic returns to step 400, as described in step 420a. In step 430a, the control logic further provides an anticipated patient status, based on the personalized patient alarm management profile and the trend. Optionally, in step 440a the control logic also provides a clinical recommendation and/or instruction to the caregiver, the patient and/or his relatives, based on the personalized patient alarm management profile and/or the anticipated medical status. Has the contextual alarm threshold value been crossed, the control logic triggers the alarm, as described in step 420b. Furthermore, in the event of an alarm, the control logic may provide a trend history of, as described in step 430b. The trend history may be based on measured medical parameters obtained during a predetermined time period prior to the alarm being triggered. Optionally, in step 440b the control logic may provide a clinical recommendation and/or instruction to the caregiver, the patient and/or his relatives, based on the personalized patient alarm management profile and/or the trend.

Figure 5:
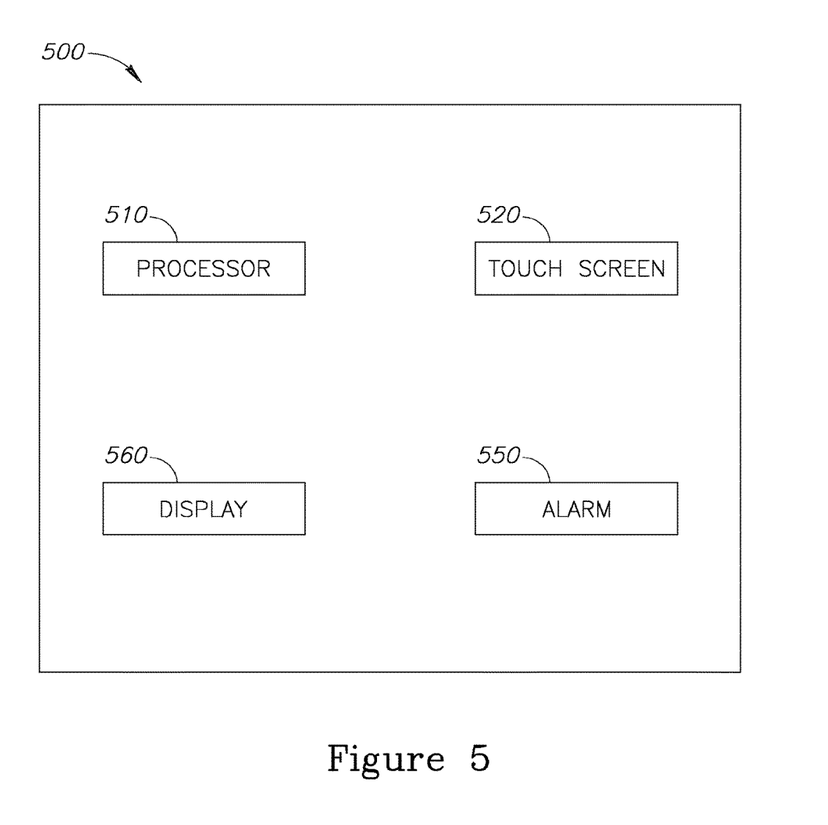
FIG. 5 schematically illustrates a medical device according to some embodiments.

Reference is now made to FIG. 5 which schematically illustrates a medical device 500 according to some embodiments. Medical device 500 includes a processor 510 having a control logic. Processor 510 is configured to receive a measured medical parameter of a patient and to compare the measured medical parameter to a contextual alarm threshold. Processor 510 is further configured to receive at least two profile determinants, to determine a personalized patient alarm management profile based on the provided threshold determinants and to determine a contextual alarm threshold based on the personalized patient alarm management profile. It is understood to the skilled in the art that the provided profile determinants may be default threshold determinants automatically provided to processor 510. Alternatively, the threshold determinants may be provided to processor 510 by a caregiver or other medical personnel through a user-interface, such as touch screen 520. Medical device 500 further includes an alarm 550 configured to be triggered when the measured medical parameter crosses the contextual alarm threshold. Medical device 500 may also include a display configured to display the measured medical parameter, such as color display 560 and/or a trend thereof. According to some embodiments, which parameters are displayed on color display 560 is determined based on the personalized patient alarm management profile. According to some embodiments, color display 560 may be configured to depict all normal values in a first color (e.g. green) and values out of range in a second color (e.g. red). Additionally or alternatively, color display 560 may be configured to depict all normal values in a first color (e.g. green). When a measured medical parameter reaches a level requiring caution, the value may turn yellow, and only when reaching an alarm (risk) level, it may turn red. Similarly, green, yellow and red colors may be used to define regions within the trend.

As described herein, the control logic may be configured to adjust the personalized patient alarm management profile and/or the contextual alarm threshold as a result of changes in one or more of the profile determinants. It is understood by one of ordinary skill in the art that such adjustment can be carried out at any stage of the operation of the control logic. For example, the adjustment may be carried out as a result of an excessive triggering of the alarm, and identification of OSA.

Figure 6A:
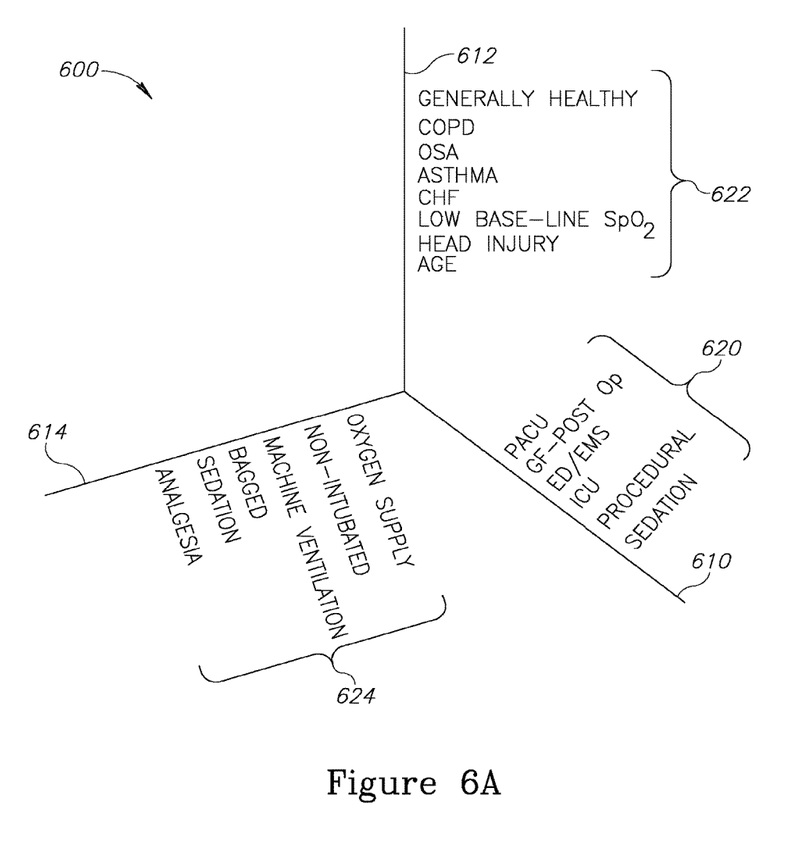
FIG. 6A schematically illustrates a user interphase for determining a personalized patient alarm management profile, according to some embodiments.
Figure 6B:
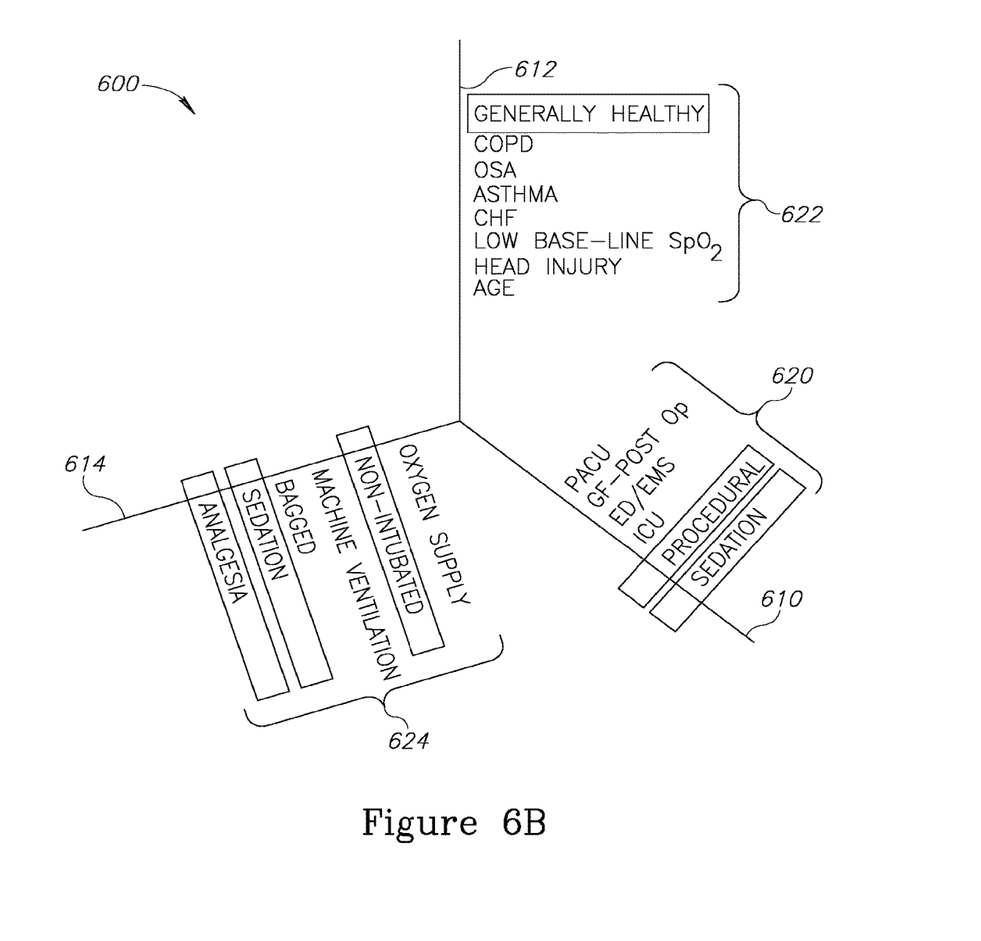
FIG. 6B schematically illustrates a user interphase for determining a personalized patient alarm management profile, according to some embodiments.

Reference is now made to FIGS. 6A and B which schematically illustrates a user interface configured to determine a personalized patient alarm management profile for use when monitoring one or more medical parameters, according to some embodiment. As shown in FIG. 6A, user interphase 600 displays the profile determinants configured to determine the personalized patient alarm management profile, here profile determinants clinical environment 610, background characteristic 612 and treatment profile 614. Each profile determinant includes user selectable options collectively referred to as user selectable options 620, 622 and 624, respectively. As shown in FIG. 6B one or more selectable options may be elected by the user for each of clinical environment 610, background characteristic 612, treatment profile 614, here procedural sedation care unit for clinical background 610, generally healthy for background characteristic 612 and non-intubated, sedation and analgesia for treatment profile 614. User interface 600 may include a processor (not shown) configured to determine the personalized patient alarm management profile based on profile determinants clinical environment 610, background characteristic 612, treatment profile 614.

As further shown in FIG. 6B, user interface 600 further displays the determined personalized patient alarm management profile including characterization of hospitalization 630 (here short term), main concern 640 (here risk of apnea and risk of low quality $CO_2$ signal), required features 650 (here presence/absence of breaths, respiration rate, $CO_2$ waveform, pleth wave and nuisance parameters), and proposed alarm profile 660 (here single parameter thresholds, index parameter.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

EXAMPLES

The following examples are presented in order to more fully illustrate some embodiments of the invention. They should, in no way be construed, however, as limiting the scope of the disclosure.

Example 1

Determining a personalized patient alarm management profile for a normally healthy patient, in a procedural sedation care unit, receiving analgesia and sedation.

As detailed hereinabove the described profile determinants are provided to a control logic. Normally healthy patients undergoing procedures requiring sedation and pain management (for example in an operating room (OR)) are characterized by a relatively short stay (in average 2 hours) during which a caregiver is constantly present.

The main concern for patients sharing these profile determinants is the risk of apnea which are usually sudden (following bolus of sedatives), hypoventilation, and low quality $CO_2$ signals (e.g., if using improper interface during endoscopy).

Accordingly, the personalized patient alarm management profile is characterized with risk of absence of breath and low respiration rate (RR). Nuisance alarms due to high respiration rate and high/low $EtCO_2$ are expected. The contextual alarm threshold should therefore preferably be set so as to trigger an alarm if any one or more of the following occurs: no-breath signal is observed for 30 sec, low RR (6 BPM for 10 sec), Low $EtCO_2$ (25 mHg for 2 min), High $EtCO_2$ (50 mmHg for 2 min), High RR (25 BPM for 2 min), Low $SpO_2$ (85% for 10 sec and/or 90% for 50 SatSec).

The $CO_2$ waveform, the pleth-wave (or other indication of $SpO_2$ quality) should preferably be displayed.

In case the patient receives oxygen supply, the contextual alarm should be adjusted to take into consideration that reduction in oxygen saturation may occur at higher saturation values. Accordingly, the Low $SpO_2$ limit should be more sensitive (for example by adjusting the limit to 90% for 10 sec and/or 92% for 25 SatSec).

Example 2

Determining a personalized patient alarm management profile for a normally healthy, non-intubated patient, in post-operative care unit, receiving analgesia.

Normally healthy patients, having undergone an operative procedure are typically hospitalized in a post-operative setting for a relatively long period of time (usually more than 4 hours) during which the patient eats, talk moves etc. A caregiver is typically not present constantly.

The main concern for patients sharing these profile determinants is the risk of apnea, the risk of very low respiration rate and high $EtCO_2$. Nuisance alarms due to disconnection of sensors are expected.

Accordingly, the personalized patient alarm management profile is characterized by a risk of absence of breath, low respiration and low saturation. The contextual alarm threshold should therefore preferably be set so as to trigger an alarm if any one or more of the following occurs: no breath signal is observed for 30 sec, Low RR (4 BPM or below for 1 min), Low $EtCO_2$ (10 mHg for 5 min), High $EtCO_2$ (60 mmHg for 5 min), High RR (40 BPM for 2 min), Low $SpO_2$ (85% for 15 sec and/or 90% for 75 SatSecs).

As the patient may from time to time disconnect the sensors (for example when eating, talking a bath or the like), an easy alerts-disable option is recommendable. Furthermore, due to the relatively long stay (often days and even weeks), the personalized patient alarm management profile and/or alarm threshold should be adjusted if OSA is indicated.

Example 3

Determining a personalized patient alarm management profile for an OSA patient in post-operative care unit, the patient being non-intubated and receiving analgesia. As described herein the OSA settings may, when known, be indicated as a threshold determinant at the beginning of the monitoring. However, OSA is often only detected during hospitalization, as a result of monitoring the patient. In such instances the personalized patient alarm management profile (patient characteristic) should be adjusted accordingly.

OSA patient are characterized by on the one hand suffering from frequent low-risk apneas which tend to cause nuisance alarms, and on the other hand by having an elevated sensitivity of the ventilatory system to the effects of analgesia which put them in a high risk group.

Upon identification of OSA in a patient, two levels of alarms may be applied. The first level triggers a notification of the patient and/or his relatives indicating that out-of-normal parameters are obtained, without triggering a traditional alarm. Such notification may for example be triggered when no breath signal is observed for 30 seconds and/or when $SO_2$ is 90% for 10 sec or 92% for 25 SatSec. The second level triggers the traditional alarm, but only when a persistent absence of breath is observed, for example, when no breath signal is observed for 60 seconds and/or when $SpO_2$ is low (90% for 15 sec and/or 92% for 75 SatSecs); or when no change is observed in response to the notification.

The invention claimed is:

1. A medical device having a processor comprising instructions configured to:
   receive a measured medical parameter of a patient, wherein the measured medical parameter comprises a $CO_2$ related parameter, a ventilation related parameter, respiration rate (RR), an oxygen related parameter, heart rate (HR), an electrocardiogram (ECG), encephalogram (EEG), blood parameter, spirometry, level of consciousness, level of sedation, or any combination thereof;
   compare the measured medical parameter or a trend of the measured medical parameter to a contextual threshold value, wherein the contextual threshold value is determined based on a personalized patient alarm management profile, wherein the personalized patient alarm management profile is based on at least two profile determinants;
   output a clinical recommendation in response to the personalized patient alarm management profile; and trigger an alarm when the measured medical parameter or the trend crosses the contextual threshold value, wherein the contextual threshold value is weighted by an incremental time factor.

2. The medical device of claim 1, wherein the processor comprises instructions configured to output an anticipated medical status based on the personalized patient alarm management profile and the measured medical parameter or the trend.

3. The medical device of claim 1, wherein the clinical recommendation is further based on the measured medical parameter or the trend when the measured medical parameter does not cross the contextual threshold value.

4. The medical device of claim 1, wherein the processor comprises instructions configured to output a history of the measured medical parameters in response to the alarm, and wherein the history of the measured medical parameters is based on the measured parameters received over a predetermined time period prior to the alarm.

5. The medical device of claim 4, wherein the clinical recommendation is further based on the history of the measured medical parameters.

6. The medical device of claim 1, wherein the processor comprises instructions configured to adjust the personalized patient alarm management profile based on a change in one or more of the at least two profile determinants.

7. The medical device of claim 1, wherein the processor comprises instructions configured to determine the trend in the measured medical parameter based on the received measured medical parameter over a predetermined time.

8. The medical device of claim 7, wherein the trend is a moving average of the measured medical parameter.

9. The medical device of claim 1, wherein the at least two profile determinants comprise a clinical environment of the patient, a background characteristic of the patient, a treatment profile of the patient, or any combination thereof.

10. A method, comprising:
receiving, at a processor, a medical parameter as measured by a medical monitoring device;
determining, using the processor, a contextual alarm threshold value based on a personalized patient alarm management profile, wherein the personalized patient alarm management profile is based on at least two profile determinants;
triggering, using the processor, an alarm in response to the medical parameter crossing the contextual threshold value, wherein the contextual threshold value is weighted by an incremental time factor;
determining, using the processor, a history of the medical parameters in response to the alarm, wherein the history of the medical parameters is based on the measured parameters received over a predetermined time period prior to the alarm; and
providing, using the processor, a clinical recommendation based on the personalized patient alarm management profile and the history of the medical parameters.

11. The method of claim 10, comprising determining a trend in the medical parameter and comparing the trend to the contextual threshold value using the processor, wherein the trend comprises a moving average of the medical parameter.

12. The method of claim 10, comprising adjusting the personalized patient alarm management profile based on a change in one or more of the at least two profile determinants.

13. The method of claim 10, wherein the at least two profile determinants comprise a clinical environment of the patient, a background characteristic of the patient, a treatment profile of the patient, or any combination thereof.

14. The method of claim 10, wherein the measured parameter comprises a $CO_2$ related parameter, a ventilation related parameter, respiration rate (RR), an oxygen related parameter, heart rate (HR), an electrocardiogram (ECG), and encephalogram (EEG), blood parameter, spirometry, level of consciousness, level of sedation, or any combination thereof.

15. A medical device having a processor comprising instructions configured to:
receive a measured medical parameter of a patient;
compare the measured medical parameter or a trend of the measured medical parameter to a contextual threshold value, wherein the contextual threshold value is determined based on a personalized patient alarm management profile, wherein the personalized patient alarm management profile is based on at least two profile determinants, wherein the at least two profile determinants comprise a clinical environment of the patient, a background characteristic of the patient, a treatment profile of the patient, or any combination thereof;
trigger an alarm when the measured medical parameter or the trend crosses the contextual threshold value, wherein the contextual threshold value is weighted by an incremental time factor; and
determine an anticipated patient status based on the personalized patient alarm management profile and the measured medical parameter or the trend when the measured medical parameter or the trend does not cross the contextual threshold value.

16. The medical device of claim 15, wherein the processor comprises instructions configured to output a clinical recommendation based on the personalized patient alarm management profile and the anticipated patient status.

17. The medical device of claim 15, wherein the processor comprises instructions configured to output a clinical recommendation based on the patient alarm management profile.

* * * * *